United States Patent [19]

Hung

[11] Patent Number: 4,604,458

[45] Date of Patent: Aug. 5, 1986

[54] 3-SUBSTITUTED CARBONYLOXY-7-DISUBSTITUTED AMINO-10-SUBSTITUTED CARBONYLPHENOTHIAZINES

[75] Inventor: William M. Hung, Cincinnati, Ohio

[73] Assignee: The Hilton-Davis Chemical Co., Cincinnati, Ohio

[21] Appl. No.: 771,875

[22] Filed: Sep. 3, 1985

Related U.S. Application Data

[62] Division of Ser. No. 636,464, Jul. 31, 1984, Pat. No. 4,551,740.

[51] Int. Cl.$^4$ ............................................. C07D 265/28
[52] U.S. Cl. ...................................................... 544/37
[58] Field of Search ............................................ 544/37

[56] References Cited

U.S. PATENT DOCUMENTS 2,909,520  10/1959  Buc ........................................ 260/243
3,704,298  11/1972  Zinnes et al. ........................... 544/49
4,309,255   1/1982  Gendler et al. ........................... 204/2
4,496,584   1/1985  Fujii et al. ......................... 560/139 X

OTHER PUBLICATIONS

Buehler et al, Survey of Organic Chemistry, 1970, Wiley-Interscience, New York, p. 264.
Mariga & Oda, Kogyo Kagaku Zasshi, 67(7), 1050-4 (1964) (C.A. 62 2852b).

Primary Examiner—Richard L. Raymond
Attorney, Agent, or Firm—Terrence E. Miesle; Thomas L. Johnson; Paul E. Dupont

[57] ABSTRACT

3-(R-Carbonyloxy)-7-(N-R$^1$-N-R$^2$-amino)-10-(RCO)-phenothiazines useful as color formers, particularly in electrochromic recording systems, are prepared by the interaction of the corresponding 7-(N-R$^1$-N-R$^2$-amino)-phenothiazin-3-one with a reducing agent to obtain the corresponding leuco compound and subsequently interacting the leuco compound with about two molecular proportions of an acylating agent.

6 Claims, No Drawings

3-SUBSTITUTED CARBONYLOXY-7-DISUBSTITUTED AMINO-10-SUBSTITUTED CARBONYLPHENOTHIAZINES

This application is a division of my copending application Ser. No. 636,464, filed July 31, 1984, and now U.S. Pat. No. 4,551,740.

BACKGROUND OF THE INVENTION (a) Field of the Invention

This invention relates to novel compounds classified in the field of organic chemistry as phenothiazines, useful as color-forming substances, particularly in the art of electrochromic recording; to electrochromic recording systems containing said compounds; and to processes for preparing said compounds.

(b) Information Disclosure Statement

Several classes of organic compounds of widely diverse structural types are known to be useful as colorless precursors for electrochromic recording. Among the more important classes, there may be named leuco-type dyestuffs such as: phthalides, for example, crystal violet lactone, Malachite green lactone; fluorans, for example, 3-diethylamino-5,7-dimethylfluoran; and indolinobenzospiropyrans, for example, 1,3,3-trimethyl-6'-chloro-8'-methoxyindolinobenzospiropyrans. Also utilized as colorless precursors for electrochromic recording, either alone or in admixture with the leuco compounds indicated above, are substances known as redox indicators. The redox indicator which becomes colored in situ in the electrochromic recording process also is generally a leuco compound. Among the types of compounds which are applicable as redox indicators are phenothiazines, for example, leuco methylene blue and benzoyl leuco methylene blue. Other specific indicators are Leucoethyl Nile Blue, Leucomethyl Capyrl Blue and Leucosafranine T. Typical of the many such electrochromic recording systems taught in the prior art are those described in U.S. Pat. Nos. 3,726,769, 3,871,972, 3,864,684, 4,017,366, 4,133,933, and U.S. Pat. No. Re. 29,427 which issued Apr. 10, 1973, Mar. 18, 1975, Feb. 4, 1975, Apr. 12, 1977, Jan. 9, 1979, and Oct. 4, 1977, respectively. The methods for electrochromic recording taught in the prior art have many variations. Basically, a sheet of paper is coated or treated on one or both sides with a coating formulation containing at least one colorless color-forming (leuco) compound. Electrical current is then selectively applied to the coated side of the paper by some means, for example, a stylus or a printing head to which an electrical potential can be applied. The application of the current causes an electrochromic reaction involving the leuco compound to produce a visible image corresponding to the design traced by the stylus or that of the printing head.

The following items to date appear to constitute the most relevant prior art with regard to the instant invention.

U.S. Pat. No. 2,909,520, issued Oct. 20, 1959, discloses compounds having the formula

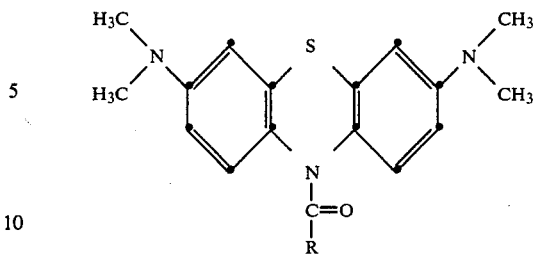

in which R is a phenyl or naphthyl groups substituted with one or more of the following moieties: alkyl, alkoxy, halo, nitro, haloalkyl, alkoxycarbonyl, phenyl, and phenylalkoxy. These compounds are disclosed as being useful as blue color formers in carbonless carbon papers, i.e., carbonless duplicating systems.

Mariga and Oda in Kogyo Kagaku Zasshi 67 (7), 1050-4 (1964) (C.A. 62 2852b) describe the preparation and properties of acylated methylene blue having the structural formula

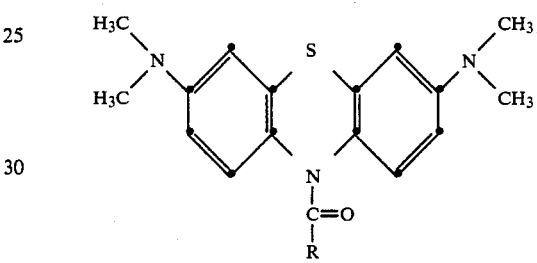

in which R represents an alkyl or a substituted phenyl moiety. The compounds are disclosed as being useful in pressure-sensitive carbonless duplicating systems.

U.S. Pat. No. 4,309,255, issued Jan. 5, 1982, discloses and claims a phenothiazone having the structural formula

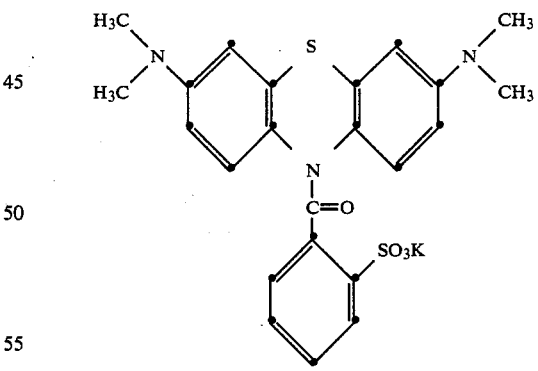

which is disclosed as being useful as a blue color former in electrochromic recording paper.

SUMMARY OF THE INVENTION

In its composition of matter aspect, the invention relates to certain 3-(R-carbonyloxy)-7-(N-$R^1$-N-$R^2$-amino)-10-acylphenothiazines useful as colorless precursors in electrochromic recording systems.

The present invention provides in its article of manufacture aspect, a substrate for use in electrochromic recording systems comprising a support sheet containing as a color-forming substance a 3-(R-carbonyloxy)-7-(N-$R^1$-N-$R^2$-amino)-10-acyl-phenothiazine.

In its process aspect, the invention relates to a process for producing 3-(R-carbonyloxy)-7-(N-$R^1$-N-$R^2$-amino)-10-acyl-phenothiazines which comprises interacting the corresponding 7-(N-$R^1$-N-$R^2$-amino)phenothiazin-3-ones with a reducing agent to obtain the corresponding leuco compound and subsequently interacting the leuco compound with at least two molecular proportions of an acylating agent.

DETAILED DESCRIPTION INCLUSIVE OF THE PREFERRED EMBODIMENTS

More specifically, this invention in its composition of matter aspect resides in the novel compounds having the structural formula

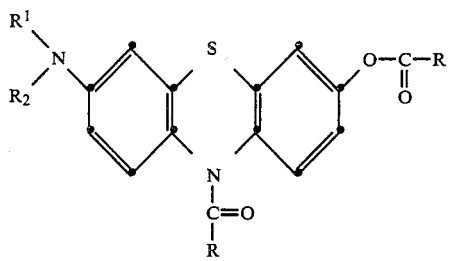

Formula I wherein R represents non-tertiary $C_1$ to $C_{12}$ alkyl, $C_4$ to $C_8$ cycloalkyl, non-tertiary $C_1$ to $C_{12}$ alkyl substituted by halogen, non-tertiary $C_1$ to $C_4$ alkoxy or non-tertiary $C_1$ to $C_4$ alkoxycarbonyl, phenyl or phenyl substituted by one to three of non-tertiary $C_1$ to $C_4$ alkyl, non-tertiary $C_1$ to $C_4$ alkoxy, nitro, halo, phenyl or cyano; and $R^1$ and $R^2$ independently represent non-tertiary $C_1$ to $C_4$ alkyl, phenyl, phenyl substituted by one or two of halo, nitro, non-tertiary $C_1$ to $C_4$ alkyl or non-tertiary $C_1$ to $C_4$ alkoxy, benzyl or benzyl substituted in the benzene ring by one or two of halo, nitro, non-tertiary $C_1$ to $C_4$ alkyl or non-tertiary $C_1$ to $C_4$ alkoxy.

Preferred compounds within the ambit of the composition of matter aspect are the novel 3-(R-carbonyloxy)-7-(N-$R^1$-N-$R^2$-amino)-10-(R-CO)-phenothiazines of Formula I wherein $R^1$ and $R^2$ are $C_1$ to $C_4$ alkyl.

In its process aspect, the invention sought to be patented resides in the process for preparing a compound according to Formula I which comprises in the first step interacting a compound having the structural formula

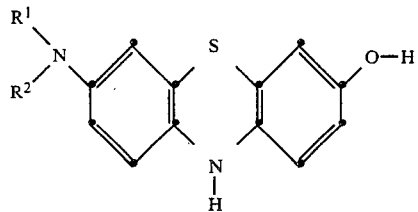

Formula II with a reducing agent to obtain the corresponding leuco compound having the structural formula

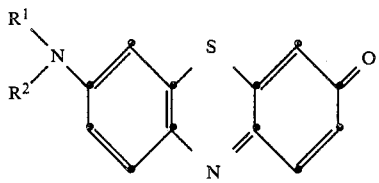

Formula III and in a second step, interacting the leuco compound with at least two molecular proportions of an acylating agent having the structural formula

R—CO—Z

Formula IV in which Z represents halo or RCOO, and R, $R^1$ and $R^2$ have the same respective meanings given in Formula I.

In its article of manufacture aspect, the invention sought to be patented resides in a substrate for use in electrochromic recording comprising a support sheet containing as a color-forming substance a phenothiazine having the structure of Formula I.

Particularly preferred within the ambit of its article of manufacture aspect is the substrate for use in electrochromic recording comprising a support sheet containing as a color-forming substance a 3-(R-carbonyloxy)-7-(dialkylamino)-10-(R-CO)-phenothiazine of Formula I wherein $R^1$ and $R^2$ represent non-tertiary $C_1$ to $C_4$ alkyl.

As used herein the terms "non-tertiary $C_1$ to $C_4$ alkyl" and "non-tertiary $C_1$ to $C_2$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, 2-ethylhexyl, nonyl, 3-ethylheptyl, n-decyl, n-undecyl, n-dodecyl and the like.

The term "non-tertiary $C_1$ to $C_4$ alkoxy" includes saturated acyclic, straight or branched-chain groups such as methoxy, ethoxy, propoxy, isopropoxy, butoxy, sec-butoxy and isobutoxy.

As used herein the terms "halo" and "halogen" include chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also satisfactory.

As used herein the term "$C_4$ to $C_8$ cycloalkyl" denotes saturated monovalent cyclic aliphatic hydrocarbon radicals including cyclobutyl, cyclopentyl, cyclohexyl, cycloheptyl, cyclooctyl and the like.

The phenothiazin-3-ones which are used as intermediates or starting materials for the compounds of Formula II are generally known compounds readily prepared by procedures well known in the art. References to the preparation of the phenothiazin-3-ones are: (a) German Pat. No. 138,255; (b) Liebig's Annalen der Chemie 251, 96, (1889); and (c) Chemische Berichte 30, 3294 (1887).

The acylating agents of Formula IV may be either aliphatic acid anhydrides or acid halides (Z=halo, preferably chloro) both of which constitute well known classes of compounds many of which are commerciallyavailable or are readily obtained by conventional synthesis well known in the art. The following list exemplifies aliphatic acid anhydrides and acid halides useful in carrying out the processes of this invention. Acetic anhydride, chloroacetic anhydride, dichloroacetic anhydride, trifluoroacetic anhydride, propionic anhydride, butyric anhydride, isobutyric anhydride, valeric anhydride, hexanoic anhydride, hepanoic anhydride, acetyl bromide, acetyl chloride, acetyl fluoride, bromoacetyl bromide, bromoacetyl chloride, chloroacetyl chloride, methoxyacetyl chloride, propionyl chloride, 2-bromopropionyl chloride, 3-bromopropionyl chloride, 2-chloropropionyl chloride, 3-chloropropionyl chloride, butyryl chloride, 4-chlorobutyryl chloride, 2-ethylbutyryl chloride, isobutyryl chloride, valeryl chloride, 5-chlorovaleryl chloride, isovaleryl chloride, 4-methylvaleryl chloride, hexanoyl chloride, 6-bromohexanoyl chloride, heptanoyl chloride, octanoyl chloride, nonanoyl chloride, decanoyl chloride, 10-undecanoyl chloride, palmitoyl chloride, myristoyl chloride, lauroyl chloride, cyclopropyl carboxylic acid chloride, cyclobutane carboxylic acid chloride, cyclohexyl carboxylic acid chloride, m-anisoyl chloride, p-anisoyl chloride, benzoyl bromide, benzoyl chloride, benzoyl fluoride, 4-biphenylcarbonyl chloride, 2-bromobenzoyl chloride, 4-bromobenzoyl chloride, 4-butoxybenzoyl chloride, 4-butylbenzoyl chloride, 2-chlorobenzoyl chloride, 3-chlorobenzoyl chloride, 4-chlorobenzoyl chloride, 4-cyanobenzoyl chloride, 2,4-dichlorobenzoyl chloride, 2,6-dichlorobenzoyl chloride, 3,4-dichlorobenzoyl chloride, 3,5-dimethoxybenzoyl chloride, 3,4-dimethoxybenzoyl chloride, 3,5-dinitrobenzoyl chloride, 2-fluorobenzoyl chloride, 3-fluorobenzoyl chloride, 4-fluorobenzoyl chloride, 3-nitrobenzoyl chloride, 4-nitrobenzoyl chloride, 2-methoxybenzoyl chloride, 3-methylbenzoyl chloride, 4-methylbenzoyl chloride, 2-iodobenzoyl chloride, 4-iodobenzoyl chloride and 4-trifluoromethylbenzoyl chloride.

The compounds of Formula I hereinabove are essentially colorless in the depicted form. When contacted with an electric current from an applied voltage stylus of the type ordinarily employed in electrochromic recording systems, the compounds of Formula I develop blue-gray, green-gray and gray-colored images. These developed images are very insensitive to light, that is, once the color is developed, it remains unchanged when subjected to light exposure. The developed images also possess excellent xerographic reproducibility.

The compounds of this invention may be incorporated in any of the commercially-accepted systems known in the electrochromic recording art. Typical techniques for the application of the color formers to paper are well known and are described in numerous patents, for example, U.S. Pat. Nos. Re. 29,427; 3,726,769; 3,864,684; 3,871,972; 3,951,757; 4,017,366; and 4,133,933. The usual paper coatings consist of the color-forming component, an organic metal salt, a binder and some type of conductor, either an inorganic salt or a conductive polymer. This mixture is milled together optionally in the presence of a non-ionic surface active agent until the desired particle size is obtained and then the mixture is coated on paper and dried. Optionally, the color-forming substance can be milled in the presence of a binder and the remaining components milled also in the presence of a binder and the two mixtures combined together prior to coating on paper. Normally the surface of the coated paper is wet with a conductive solution containing an inorganic alkali metal or alkaline earth metal salt, for example, potassium chloride, calcium chloride, sodium chloride, sodium bromide, potassium bromide, potassium nitrate or sodium sulfate immediately prior to the printing with the applied voltage stylus. For a quick qualitative test, it has been determined that the color-forming component can be dissolved in a suitable volatile organic solvent, coated on paper and the coated paper dried to obtain a paper sheet coated with the color-forming component. This coated sheet can then be wet with a conductive salt solution and an image traced with an applied voltage stylus to develop the colored image.

The compounds of Formula I can be used alone as color-forming components in electrochromic recording paper or can be used in admixture with one or more other color-forming compounds from the classes consisting of phthalides, for example, Crystal Violet Lactone; fluorans, for example, 3-diethylamino-5,7-dimethylfluoran; redox indicators, for example, phenothiazines such as benzoyl leuco methylene blue and various other types of color-forming components currently employed in commercially-accepted electrochromic recording systems.

The best mode contemplated by the inventors of carrying out this invention will now be described so as to enable any person skilled in the art to which it pertains to make and use the same.

In accordance with the aforementioned process aspect of this invention, the compounds of Formula I are obtained by reacting approximately one molecular proportion of a leuco compound of Formula III with about two molecular proportions of an acylating agent of Formula IV. When using an anhydride as the acylating agent, the reaction is conveniently carried out in an excess of the acylating agent which is utilized as both the reaction medium and as the reactant. Optionally a small amount of an organic base, for example, pyridine may be used as a catalyst. The reaction is conveniently carried out at a temperature in the range of 90° C. to reflux of the mixture for periods of approximately thirty minutes to approximately four hours. The compounds of Formula I thus obtained are isolated by pouring the reaction mixture into ice water and extracting the desired products into a suitable water immiscible organic liquid, for example, toluene. The organic liquid layer containing the product is subsequently washed with water to remove inorganic salts and water-soluble organics and then treated with decolorizing charcoal, if desired. The resulting organic liquid solution of the product is then concentrated by conventional means such as evaporation or distillation.

Alternatively, the compounds of Formula I can also be obtained by reacting one molecular proportion of a leuco compound of Formula III with at least two molecular proportions of an acyl halide (Formula IV, Z=halo). A water immiscible organic liquid solution, for example, toluene, containing the leuco compound is heated to a temperature in the range of 60° to 80° C. and disodium phosphate and acyl halide, dissolved in the same organic liquid, are added. The reaction is conveniently carried out at the reflux temperature of the mixture for periods of approximately fifteen minutes to approximately nineteen hours. Water and additional disodium phosphate are added to the reaction mixture and the resulting mixture is heated at reflux temperature for a period of approximately thirty minutes to approximately one hour. The organic liquid solution containing the desired product is separated from the water layer, washed with water and concentrated by conventional means such as evaporation or distillation. The isolated product can be purified by conventional means such as recrystallization or reslurrying with a suitable organic liquid and then collected by filtration. A less conventional yet still acceptable method of purification is to subject the product needing purification to separation by column chromatography. The material to be purified is dissolved in a suitable organic liquid and the solution is passed through a chromatography column which has been packed with a suitable substrate, for example, silica gel, cellulose, alumina and the like. Numerous fractions are collected and analyzed to determine fraction(s) containing the desired product. The fraction(s) which contain the desired product are then combined (if more than one) and concentrated to obtain the product. The leuco compound of Formula III is conveniently prepared by reducing the corresponding phenothiazin-3-one of Formula II with a reducing agent, for example, zinc powder or an alkali hydrosulfite. When zinc dust is used as the reducing agent, the reaction is conveniently carried out in an excess of the anhydride acylating agent simultaneously performing as the reaction medium for the reduction and as the acylating agent without the need for an inert organic liquid reaction medium. When the hydrosulfite is used as the reducing agent, the leuco compound prepared is conveniently carried out in a mixture of water and a suitable water immiscible organic liquid, for example, toluene or xylene in an inert atmosphere, for example, nitrogen. The reaction is carried out in the presence of an alkaline substance, for example, sodium carbonate or disodium phosphate using, as the reducing agent, an alkali hydrosulfite, for example, sodium hydrosulfite. The reaction is conveniently carried out at ambient temperature for a period of approximately fifteen minutes to approximately two hours. The organic liquid solution which contains the leuco compond is separated from the water layer. Additional alkali hydrosulfite is added to the organic liquid solution and the resulting mixture is azeotroped to remove the remaining traces of water. This solution containing the leuco compound is then used in the acylating step of the process as described above.

The molecular structures of the compounds were assigned on the basis of the modes of synthesis and a study of their infrared, nuclear magnetic resonance and mass spectra.

The following examples will further illustrate the invention without, however, limiting it thereto.

EXAMPLE 1

Under a nitrogen atmosphere, a mixture of 5.0 g of 7-dimethylaminophenothiazin-3-one (commercially known as methylene violet), 75.0 ml of acetic anhydride, 5.0 ml of pyridine and 5.0 g of zinc dust was maintained at reflux temperature for approximately three hours. After cooling to room temperature, the reaction mixture was filtered to remove the insolubles and the filter cake was washed twice, each time with 50.0 ml of acetone. The combined filtrate and acetone washes was poured slowly into water and toluene was added to the resulting mixture. After stirring for approximately thirty minutes, the layers were separated and the water layer was discarded. The organic extract was treated with activated charcoal, filtered and the toluene was removed by evaporation at reduced pressure to obtain a gummy residue. The residue was dissolved with ethyl acetate and the resulting solution was passed through a chromatography column packed with silica gel using ethyl acetate to elute the column. The first four fractions were combined, concentrated, and the solid which formed was collected by filtration and dried to obtain 2.6 g of 7-dimethylamino-3-acetyloxy-10-acetylphenothiazine (Formula I: $R=R^1=R^3=CH$), a white powder which melted at 124° to 128° C. The mass spectrum showed significant maxima at 342 (M+) and 299 (M+—$CH_3CO$). Paper coated with an ink formulation containing the product produced a blue-gray-colored image when contacted with an applied voltage stylus.

EXAMPLE 2

A mixture of 16.0 g of 7-dimethylaminophenothiazin-3-one, 400.0 ml of water, 400.0 ml of toluene, 15.0 g of sodium carbonate and 20.0 g of sodium hydrosulfite was stirred at approximately 40° C. for approximately thirty minutes. The aqueous layer was separated from the toluene solution and discarded. To the toluene solution there was added 15.0 g of sodium hydrosulfite and 200.0 ml of toluene. The residual water was azeotroped from the toluene solution. The resulting solution was cooled to approximately 70° C. and 15.0 g of disodium phosphate and 30.0 ml of benzoyl chloride dissolved in 70.0 ml of toluene was added. The resulting mixture was maintained at reflux temperature for approximately two hours. The reaction mixture was cooled to room temperature and slowly poured into 400.0 ml of ice water. The reaction vessel was rinsed twice, once with 200.0 ml of toluene and once with 200.0 ml of water. The water layer was separated and discarded. The toluene solution was washed six times as follows: twice, each with 300.0 ml of water; twice, each with 300.0 ml of five percent aqueous sodium carbonate solution; once with 400.0 ml of water; and once with saturated aqueous sodium chloride solution. The washed toluene solution was evaporated to dryness under reduced pressure and the residue recrystallized from a mixture of isopropanol and hexane. The resulting solid was then reslurried in 75.0 ml of hot isopropanol and filtered to obtain 1.8 g of a white solid. This solid was reslurried in 50.0 ml of isopropanol, 25.0 ml of water and 1.0 g of disodium phosphate at a temperature in the range of 60° to 70° C. for approximately fifteen minutes, cooled and the solid was collected by filtration and dried to obtain 1.28 g of 7-dimethylamino-3-benzoyloxy-10-benzoylphenothiazine (Formula I: $R=C_6H_5$; $R^1=R^2=CH_3$), a white-colored powder which melted at 194° to 200° C. with decomposition. A significant infrared maximum appeared at 1670 cm$^{-1}$ (C=O;s). The nuclear magnetic resonance spectrum was in accord with the assigned structure. The mass spectrum showed significant maxima at 466 (M+) and 361 (M+—$C_6H_5CO$). Paper coated with an ink formulation containing the product produced a gray-colored image when contacted with an applied voltage stylus.

EXAMPLE 3

Proceeding in a manner similar to the one described in Example 2 above, 10.0 g of 7-dimethylamino-3-phenothiazin-3-one was interacted with 15.0 g of sodium hydrosulfite to obtain the leuco compound which was subsequently reacted with 25.0 ml of para-anisoyl chloride to obtain after purification utilizing column chromatography and recrystallization from a mixture of hexane and acetone, 0.56 g of 7-dimethylamino-3-(4-methyloxybenzoyloxy)-10-(4-methoxybenzoyl)phenothiazine (Formula I: R=4—CH$_3$OC$_6$H$_4$; R$^1$=R$^2$=CH$_3$), a white solid which melted at 149° to 150° C. A significant infrared maximum appeared at 1670 cm$^{-1}$ (C=O;s). Paper coated with an ink formulation containing the product produced a green-gray-colored image when contacted with an applied voltage stylus.

EXAMPLE 4

Following the procedure described in Example 1 above, 7.0 g of 7-dimethylamino-3-phenothiazin-3-one was interacted with 5.0 g of zinc dust to obtain the leuco compound which was subsequently interacted with 50.0 ml of butyric anhydride in the presence of 5.0 ml of pyridine to obtain after purification utilizing column chromatography, 3.57 g of 7-dimethylamino-3-butyryloxy-10-butyrylphenothiazine (Formula I: R=C$_3$H$_7$; R$^1$=R$^2$=CH$_3$), a pale brown gum. A significant infrared maximum appeared at 1680 cm$^{-1}$ (C=O;s). Paper coated with an ink formulation of the product produced a blue-gray-colored image when contacted with an applied voltage stylus.

It is contemplated that by following the procedure described in the foregoing examples, but employing the appropriate 7-(N-R$^2$-N-R$^3$-amino)phenothiazin-3-ones of Formula II with a reducing agent and the appropriate acylating agent of Formula IV, there will be obtained 3-(R-carbonyloxy)-7-(N-R$^2$-N-R$^3$-amino)-10-(R-CO)-phenothiazine of Formula I, presented in Examples 5 to 23 in Table A hereinbelow.

TABLE A

| Example No. | R | R$^1$ | R$^2$ |
| --- | --- | --- | --- |
| 5 | ClCH$_2$ | C$_6$H$_5$CH$_2$ | C$_6$H$_5$CH$_2$ |
| 6 | CH$_3$OCH$_2$ | C$_2$H$_5$ | CH$_3$ |
| 7 | C$_3$H$_5$ | C$_6$H$_5$ | CH$_3$ |
| 8 | Cl$_2$CH | C$_4$H$_9$ | C$_4$H$_9$ |
| 9 | C$_5$H$_{11}$ | 4-CH$_3$C$_6$H$_4$CH$_2$ | 4-CH$_3$C$_6$H$_4$CH$_2$ |
| 10 | BrCH$_2$ | 4-NO$_2$C$_6$H$_4$CH$_2$ | CH$_3$ |
| 11 | 2-BrC$_2$H$_4$ | CH$_3$ | C$_6$H$_5$ |
| 12 | 2-BrC$_2$H$_4$ | 3-ClC$_6$H$_4$CH$_2$ | C$_2$H$_5$ |
| 13 | 3-ClC$_3$H$_6$ | C$_4$H$_9$ | C$_4$H$_9$ |
| 14 | 2-(C$_2$H$_5$)C$_3$H$_6$ | C$_2$H$_5$ | 3-BrC$_6$H$_4$CH$_2$ |
| 15 | 5-C$_5$H$_{10}$ | 2,4-Cl$_2$C$_6$H$_3$CH$_2$ | CH$_3$ |
| 16 | C$_{11}$H$_{23}$ | C$_2$H$_5$ | 2,3-(CH$_3$)$_2$C$_6$H$_3$CH$_2$ |
| 17 | C$_3$H$_5$ | 2,5-(CH$_3$)$_2$C$_6$H$_3$CH$_2$ | C$_2$H$_5$ |
| 18 | 4-C$_4$H$_9$OC$_6$H$_4$ | 2,6-Cl$_2$C$_6$H$_3$CH$_2$ | CH$_3$ |
| 19 | 4-C$_4$H$_9$C$_6$H$_4$ | 2-FC$_6$H$_4$CH$_2$ | C$_4$H$_9$ |
| 20 | 2,4-Cl$_2$C$_6$H$_3$ | 2-CH$_3$C$_6$H$_4$CH$_2$ | 2-CH$_3$C$_6$H$_4$CH$_2$ |
| 21 | 3,5-(CH$_3$O)$_2$C$_6$H$_3$ | 4-CH$_3$C$_6$H$_4$CH$_2$ | C$_2$H$_5$ |
| 22 | 3,5-(NO$_2$)$_2$C$_6$H$_3$ | C$_2$H$_5$ | C$_2$H$_5$ |
| 23 | 2-IC$_6$H$_4$ | CH$_3$ | CH$_3$ |

What is claimed is:

1. A compound having the structural formula

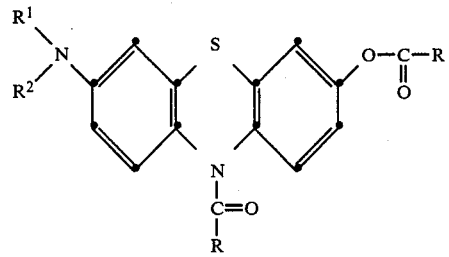

wherein:

R represents non-tertiary C$_1$ to C$_{12}$ alkyl, C$_4$ to C$_8$ cycloalkyl, non-tertiary C$_1$ to C$_{12}$ alkyl substituted with halogen, non-tertiary C$_1$ to C$_4$ alkoxy or non-tertiary C$_1$ to C$_4$ alkoxycarbonyl, phenyl or phenyl substituted by one to three of non-tertiary C$_1$ to C$_4$ alkyl, non-tertiary C$_1$ to C$_4$ alkoxy, nitro, halo, phenyl or cyano; and R$^1$ and R$^2$ independently represent non-tertiary C$_1$ to C$_4$ alkyl, phenyl, phenyl substituted by one or two of halo, nitro, non-tertiary C$_1$ to C$_4$ alkyl or non-tertiary C$_1$ to C$_4$ alkoxy, benzyl or benzyl substituted in the benzene ring by one or two of halo, nitro, non-tertiary C$_1$ to C$_4$ alkyl or non-tertiary C$_1$ to C$_4$ alkoxy.

2. A 3-(R-carbonyloxy)-7-(N-R$^1$-N-R$^2$-amino)-10-(R-CO)-phenothiazine according to claim 1 in which R$^1$ and R$^2$ are C$_1$ to C$_4$ alkyl.

3. 7-(Dimethylamino)-3-(acetyloxy)-10-acetylphenothiazine according to claim 2.

4. 7-(Dimethylamino)-3-(benzoyloxy)-10-(benzoyl)-phenothiazine according to claim 2.

5. 7-(Dimethylamino)-3-(4-methoxybenzoyloxy)-10-(4-methoxybenzoyl)phenothiazine according to claim 2.

6. 7-(Dimethylamino)-3-(butyryloxy)-10-(butyryl)-phenothiazine according to claim 2.

* * * * *